United States Patent [19]

Aebischer et al.

[11] Patent Number: 5,030,225
[45] Date of Patent: Jul. 9, 1991

[54] ELECTRICALLY-CHARGED NERVE GUIDANCE CHANNELS

[75] Inventors: Patrick Aebischer, Barrington; Robert F. Valentini, Warwick, both of R.I.

[73] Assignee: Brown University Research Foundation, Providence, R.I.

[21] Appl. No.: 621,081

[22] Filed: Nov. 30, 1990

Related U.S. Application Data

[63] Continuation-in-part of Ser. No. 272,555, Nov. 17, 1988, and a continuation-in-part of Ser. No. 585,285, Sep. 17, 1990, which is a continuation-in-part of Ser. No. 25,529, May 13, 1987, abandoned.

[51] Int. Cl.$^5$ .................... A61B 17/00; A61F 2/00
[52] U.S. Cl. ..................... 606/152; 623/12; 623/25
[58] Field of Search ............ 606/152; 623/12, 24, 623/25

[56] References Cited

U.S. PATENT DOCUMENTS

| | | | |
|---|---|---|---|
| 3,786,817 | 1/1974 | Palma | 128/334 R |
| 3,833,002 | 9/1974 | Palma | 128/334 R |
| 3,893,462 | 7/1975 | Manning | 128/421 |
| 3,916,905 | 11/1975 | Kuhn | 128/334 R |
| 3,925,339 | 12/1975 | Ishii et al. | 260/92.1 |
| 3,960,151 | 6/1976 | Kuhn | 128/334 R |
| 3,960,152 | 6/1976 | Augurt et al. | 128/335.5 |
| 3,968,790 | 7/1976 | Fukada et al. | 128/82.1 |
| 3,988,411 | 10/1976 | Capozza | 264/184 |
| 4,033,938 | 7/1977 | Augurt et al. | 260/78.3 R |
| 4,074,366 | 2/1978 | Capozza | 3/1 |
| 4,268,653 | 5/1981 | Uchidoi et al. | 526/255 |
| 4,481,353 | 11/1984 | Nyilas et al. | 528/303 |
| 4,534,349 | 8/1985 | Barrows | 128/334 R |
| 4,662,884 | 5/1987 | Stensaas | 623/12 |
| 4,668,449 | 5/1987 | Soni et al. | 264/22 |
| 4,778,467 | 10/1988 | Stensaas et al. | 623/12 |
| 4,878,913 | 11/1989 | Aebischer et al. | 623/12 |

FOREIGN PATENT DOCUMENTS

0261833  2/1988  European Pat. Off. .
2442713  6/1980  France .

OTHER PUBLICATIONS

Midgley et al., (1968), Surgical Forum 19:519-520.
Jaffe et al., (1979), J. Exp. Zool. 29:115-128.
Fukada "Piezoelectricity of Bone" in *Mechanisms of Growth Control*, (Becker et al., eds) Springfield, MD, (1981), pp. 192-210.
Lundborg et al. (1982) J. Neuropath. Exper. Neurol. 41:412-422.
Molander et al. (1982) Muscle & Nerve 5:54-57.
Patel et al. (1982) J. Nerosci. 2:483-496.
De Rossi et al. (1983) ASAIO Journal 5:1-11.
Ito et al. (1983) Clinical Orthopaedics and Related Research No. 181, (J. B. Lippincott Co.), pp. 283-290.
Nix et al. (1983) Brain Res. 272:21-25.
Nyilas et al. (1983) Trans. Am. Soc. Artif. Intern. Organs XXIX:307-313.
Raji et al. (1983) J. Bone and Joint Surg. pp. 478-492.
Seckel et al. (1983) Plastic & Reconstruc. Surg. 74:173-181.
Uzman et al. (1983) J. Neurosci. Res. 9:325-338.
Patel et al. (1984) J. Neurosci. 4:2939-2947.
da Silva et al. (1985) Brain Res. 342:307-315.
Kerns et al. (1986) Soc. Neurosci. Abstract, vol. 12, p. 13.
Ducker et al. (1967) "Experimental Improvements in the Use of Silastic Cuff for Peripheral Nerve Repair" in *Improvements in Silastic Cuffing*, pp. 582-587.

*Primary Examiner*—Stephen C. Pellegrino
*Assistant Examiner*—Gary Jackson
*Attorney, Agent, or Firm*—Thomas J. Engellenner; Ann-Louise Kerner

[57] ABSTRACT

A medical device is disclosed for use in regenerating a severed nerve. The device includes an implantable, tubular, electrically-charged membrane having openings adapted to receive the ends of the severed nerve and a lumen having a diameter ranging from about 0.5 millimeters to about 2.0 centimeters to permit regeneration of the nerve therethrough. The membrane is fabricated such that an electric charge is exhibited at the inner membrane surface to stimulate regeneration by axonal sprouting and process extension. Also disclosed are methods for repairing a severed nerve and for preparing a medical device for use in regeneration of a severed nerve.

50 Claims, 7 Drawing Sheets

ELECTRICALLY-CHARGED NERVE GUIDANCE CHANNELS

CROSS REFERENCE TO RELATED APPLICATION

This application is a continuation-in-part of U.S. patent application Ser. No. 272,555, filed Nov. 17, 1988, and a continuation-in-part of U.S. patent application Ser. No. 585,285, filed Sept. 17, 1990, which is a continuation of U.S. patent application Ser. No. 025,529, filed Mar. 13, 1987, now abandoned.

BACKGROUND OF THE INVENTION

The technical field of this invention concerns medical devices useful for the repair of severed nerves and methods for fabricating and using such devices for nerve repair.

The problem of repairing severed nerves is a long-standing one that has plagued surgeons for over a hundred years. Despite advances in microsurgical techniques, a patient's recovery from a serious wound is often limited by a degree of nerve damage which cannot be repaired. The replanting of amputated fingers and limbs is especially limited by poor nerve regeneration.

When a nerve is severed, the functions supplied by that nerve, both motor and sensory, are lost. The appendages of the nerve cells (neurites or axons) in the distal regions of the severed nerve, or those areas furthest from the spinal cord, degenerate and die, leaving only the sheaths in which they were contained. These, too, degenerate with time. The axons in the proximal stump that remain connected to the spinal cord or dorsal root ganglion also suffer some degeneration.

However, degeneration generally does not proceed to the death of all of the nerve cell bodies. Moreover, if the injury occurs far enough from the nerve cell bodies, regeneration will occur. Regeneration of nerves does not normally include proliferation of nerve cells; rather, the injured nerve cell will grow "sprouts" from the tip of its severed axon (or nerve cell process). These axonal sprouts extend and grow distally and attempt to reenter the intact neurilemmal sheaths of the distal portion of the severed nerve. If entry is successfully made, axonal growth will continue down these sheaths, and function will eventually be restored.

In the conventional approach to nerve repair, an attempt is made to align the cut ends of the fascicles (nerve bundles within the nerve trunk). A similar approach is taken with smaller nerves. In either case, the chief hazard to the successful repair is the trauma produced by the manipulation of the nerve ends and the subsequent suturing to maintain alignment. The trauma appears to stimulate the growth and/or migration of fibroblasts and other scar-forming, connective tissue cells. The scar tissue prevents the regenerating axons in the proximal stump from reaching the distal stump to reestablish a nerve charge pathway. The result is a permanent loss of sensory or motor function.

Various attempts have been made over the years to find a replacement for direct (i.e., nerve stump-to-nerve-stump) suturing. Much of the research in this field has focused on the use of "channels" or tubular prosthesis which permit the cut ends of the nerve to be gently drawn into proximity and secured in place without undue trauma. It is also generally believed that such channels can also prevent, or at least retard, the infiltration of scar-forming, connective tissue.

For example, the use of silastic cuffs for peripheral nerve repair was reported by Ducker et al. in Vol. 28, *Journal of Neurosurgery.* pp. 582–587 (1968). Silicone rubber sheathing for nerve repair was reported by Midgley et al. in Vol. 19, *Surgical Forum*, pp. 519–528 (1968) and by Lundborg et al. in Vol. 41, *Journal of Neuropathology in Experimental Neurology.* pp. 412–422 (1982). The use of bioresorbable polyglactin mesh tubing was reported by Molander et al. in Vol. 5, *Muscle & Nerve.* pp. 54–58 (1982). The use of semipermeable acrylic copolymer tubes in nerve regeneration was disclosed by Uzman et al. in Vol. 9, *Journal of Neuroscience Research.* pp. 325–338 (1983). Bioresorbable nerve guidance channels of polyesters and other polymers have been reported by Nyilas et al. in Vol. 29, *Transactions Am. Soc. Artif. Internal Organs.* pp. 307–313 (1983) and in U.S. Pat. No. 4,534,349 issued to Barrows in 1985.

Despite the identification of various materials which can serve as nerve guidance channels, the results of research to date have revealed significant shortcomings in such prosthesis. For example, some of the materials identified above have lead to inflammatory reactions in the test animals, and have failed to exclude scar tissue formation within the channels. The total number of axons, the number of myelinated axons, the thickness of the epineurial, and the fascicular organization of nerves regenerated within guidance channels are all typically less than satisfactory and compare poorly with the original nerve structure of the test animals. Moreover, the loss of sensory or motor function is still the most common outcome of such laboratory experiments.

Electrical currents (such as DC stimulation or the application of pulsed electrical currents) directly applied to a nerve have been reported to enhance regeneration in experimental animals. For example, electrical currents produced by electrode cuffs, connected to an extracorporeal power source, and fitted to a silicone channel, have been tried to enhance peripheral nervous system (PNS) regeneration in vivo (see, Kerns et al. (1986) *Soc. Neurosci. Abstr.* Vol. 12, pp. 13) and central nervous system (CNS) regeneration (see, European Patent Application Pub. No. 261,833 by Zanakis et al.). However, such devices are bulky, typically requiring an external power supply and electrode leads penetrating through the skin and, therefore, are difficult to maintain.

Moreover, the effectiveness of such electric current-generating devices for nerve regeneration over a gap produced by resection (i.e., removal) of a nerve segment has not been demonstrated, and their effectiveness for regeneration of transected (i.e., cut) nerves has been questioned recently. See, for example, a study by M. E. McGinnis, Abstract No. 479.2, The Society for Neuroscience 20th Annual Meeting (1990) St. Louis, Mo., in which an attempt was made to repeat the experiments reported by Zanakis and others without success. In the McGinnis study, a silicone tube with electrodes at each end was used as a nerve guidance channel. The application of a current from one electrode to another for 12 days led to no difference in neurofilament positive profiles, or myelinated or unmyelinated nerve fiber density.

There exists a need for more effective nerve guidance channels which would enable the restoration of motor and/or sensory function. Materials and methods for nerve repair that would minimize surgical trauma, maximize the distance over which nerve cell processes will regenerate and the amount of neural tissue regrowth, prevent interference with nerve growth by scar tissue, and improve the chances for successful recovery of sensory or motor function. This would satisfy a long-felt need in this field.

SUMMARY OF THE INVENTION

The present application discloses improved medical devices for use as guidance channels in the repair of severed or otherwise damaged nerves. The devices includes an implantable, tubular, electrically-charged membrane having openings adapted to receive the ends of said severed nerve. The lumen of the tubular membrane preferably has a diameter ranging from about 0.5 millimeters to about 2.0 centimeters to permit the nerve to regenerate through it. The membrane is fabricated such that an electrical charge is exhibited at its inner surface to stimulate regeneration by axonal sprouting and process extension.

The term "nerve" is used herein to mean both monofascicular and polyfascicular nerves. The same general principles of regeneration within the nerve guidance channels of the present invention are applicable to both.

The thickness of the membrane may range from about 0.05 to about 1.0 millimeter. It preferably is permeable to solutes having a molecular weight of about 100,000 daltons or less. In some embodiments, this membrane is impermeable to fibroblasts and other scar-forming connective tissue cells. It may also be composed of a biodegradable material.

In one aspect of the invention, the membrane includes an electret material. The term "electret," as used herein, is intended to broadly encompass natural materials and synthetic materials displaying surface electrical charge storage capabilities. Electret materials are disclosed which can be poled to obtain nerve guidance channels displaying persistent, surface charges. These materials generate surface electrical charges which greatly augment the ability of the severed nerve ends to bridge the gap therebetween.

The electret material is polarized such that a positive or negative charge (or a combination thereof) is generated at the inner surface of the tubular membrane of the device. In one aspect of the invention, the membrane has an average charge density of about 1 to 100 nanoColoumbs/cm$^2$. Useful electret materials include polytetrafluoroethylene (PTFE), polylvinylchloride, polyethylene, polyamides, polymethyl methacrylate, polypropylene, polyethylene terapthalate, or mixtures thereof. A preferred electret material is PTFE.

In an alternative embodiment of the invention, piezoelectric materials, one class of electrets, are used to form the nerve guidance channel of the present invention. The term "piezoelectric materials" as used herein is intended to encompass natural and synthetic materials capable of generating electrical charges on their surface when subjected to mechanical strain. The preferred materials are biocompatible, semicrystalline polymers which can be poled during manufacture or prior to use in order to align the polymeric chain segments in a particular orientation and, thereby, establish a predefined dipole moment. The piezoelectric materials of the present invention are preferably poled to establish a charge generation (polarization constant) ranging from about 0.5 to about 35 picoColoumbs per Newton, and, more preferably, from about 1 to about 20 picoColoumbs per Newton.

Piezoelectric materials useful in the present invention include a variety of halogenated polymers, copolymers and polymer blends. The halogenated polymers include polyvinylidene fluoride, polyvinyl fluoride, polyvinyl chloride and derivatives thereof as well as copolymers such as copolymers of the above materials and trifluoroethylene. Non-halogenated piezoelectric polymers which may also be useful in the present invention include collagen, nylon 11, and alpha-helical polypeptides such as polyhydroxybutyrate, poly-γ-benzyl-glutamate and poly-γ-methyl-glutamate. In some applications it may also be possible to use thin piezoelectric ceramics, such as barium titanate, lead titanate or lead zirconate, or combinations of these or other ceramics with polymeric materials.

Polyvinylidene fluoride ("PVDF" or "PVF$_2$") is a particularly preferred piezoelectric material for nerve guidance channels, especially after it has been poled to impart a high polarization constant. PVDF is a semicrystalline polymer formed by the sequential addition of $(CH_2-CF_2)n$ repeat units, where n can range from about 2,000 to about 15,000.

Crystallographers have described various stable forms or phases of PVDF. The alpha phase, which is generally obtained by cooling the melt at atmospheric pressure, has a monoclinic unit cell with chain segments in antipolar orientation, and thus no net dipole moment. The beta phase of PVDF, which displays the highest piezoelectric activity, has an orthorhombic unit cell containing two chains with the same orientation, giving it a permanent dipole moment. To display its piezoelectric properties, PVDF must be anisotropic, i.e., its electrical properties must be quantitatively different for mechanical excitation along different axes. In PVDF as well as other semicrystalline polymer films, the isotropy that generally prevails can be altered by a "poling" process or molecular orientation, usually induced by mechanical stretching, followed by alignment of the permanent dipoles in a direction perpendicular to the plane of the film by an electric field. Upon mechanical deformation, such a polarized piezoelectric material will generate charge.

The invention further encompasses methods of repairing a severed nerve using the medical device as a nerve guidance channel. In these methods, the cut ends of the nerve are placed in proximity to each other within the lumen of the tubular membrane or channel and secured thereto. These nerve ends may be so secured by suturing, by friction, or with an adhesive. After the nerve ends have joined, the tube may be split along a line of weakness and removed. Alternatively, a device having a biodegradable membrane may be allowed to biodegrade in vivo.

In some embodiments of the invention, the lumen of the tubular membrane is filled with saline, a matrix material such as laminin, collagen, or growth factors, glycosaminoglycan, or nerve-related cells such as Schwann cells, before the nerve ends are secured within the device.

Methods of preparing the device useful in the regeneration of a severed nerve are also disclosed. These include fabricating a tubular membrane from a polymeric material having a polarizable molecular structure, and then poling the membrane to produce an electric charge at the inner membrane surface.

The invention will next be described in connection with certain preferred embodiments; however, it should be clear that various changes, additions and subtractions can be made by those skilled in the art without departing from the spirit or scope of the invention.

For example, although the nerve guidance channels described in the examples below are generally tubular in shape, it should be clear that various alternative shapes can be employed. The lumens of the guidance channels can be oval or even square in cross-section. The guidance channels can also be constructed from two or more parts which are clamped together to secure the nerve stumps. Moreover, polymeric, electret sheet materials can be employed and formed into channels in situ. In such a procedure, the nerve stumps can be placed on top of the sheet and then secured thereto by sutures, adhesives, or friction. The sheet can then be wrapped around the nerve segments, and the resulting channel closed by further sutures, adhesives, or friction.

BRIEF DESCRIPTION OF THE DRAWINGS

The foregoing and other objects of the present invention, as well as the various features thereof, and the inventions thereof, may be more fully understood from the following description when read together with the accompanying drawing in which.

DETAILED DESCRIPTION

Figure 1:
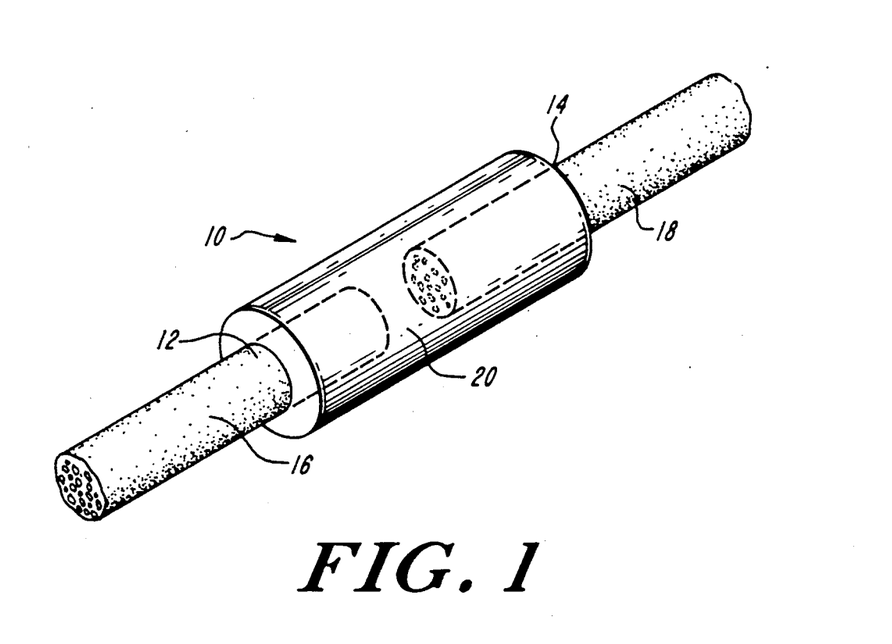
FIG. 1 is a schematic representation of a nerve guidance channel of the present invention.
Figure 2A:
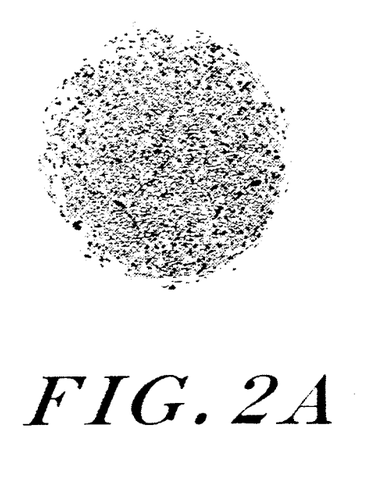
FIG. 2 is a series of electron micrographs of toluidine blue-stained transverse sections of nerves regenerated at the midpoint of an electret channel including unpoled (A and B), negatively poled (C and D), and positively poled (E and F) PTFE four weeks post-implantation. (B), (D), and (F) are higher power micrographs of the nerves shown at lower power in (A), (C), and (E), respectively.
Figure 2B:
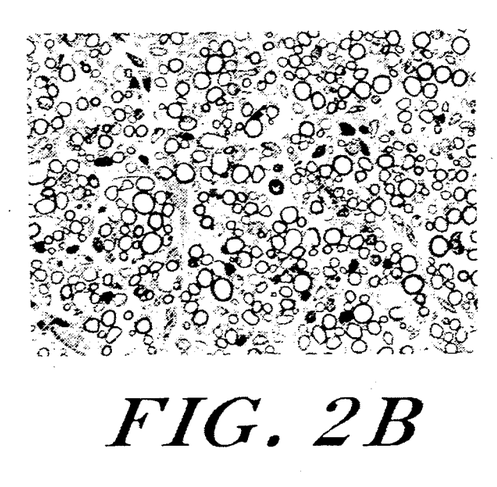
Figure 2C:
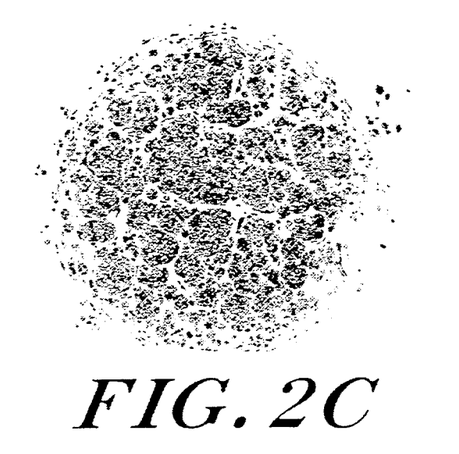
Figure 2D:
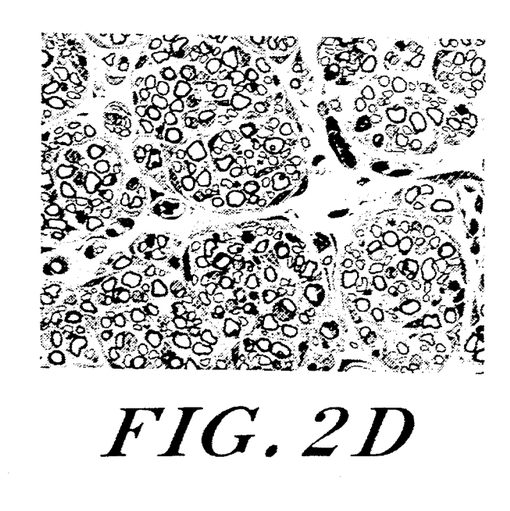
Figure 2E:
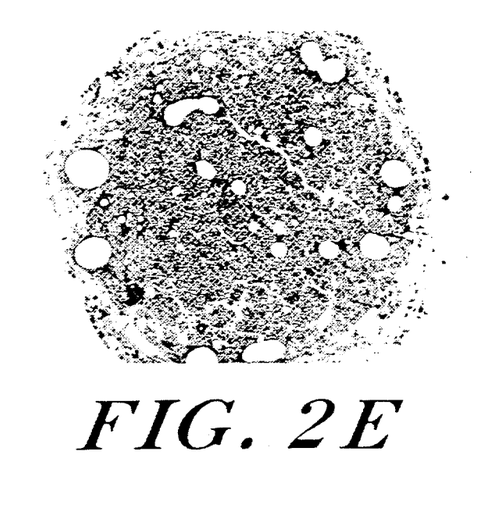
Figure 2F:
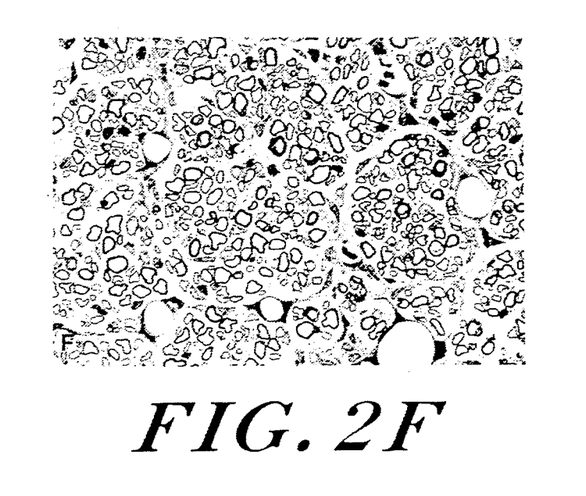

The nerve guidance channels of the present invention, an example of which is shown in FIG. 1, are composed of a tubular membrane 10 having openings 12 and 14 adapted to receive severed nerve ends 16 and 18 into lumen 20.

Preferably, the thickness of the membrane wall ranges from about 0.05 to about 1.0 millimeters (mm). Lumen 8 has a diameter which can range from about 0.5 mm to about 2.0 centimeters (cm), depending upon the size of nerve to be repaired.

The membrane is composed of an electrically-charged material which has been fabricated such that an electric charge is exhibited at the inner membrane surface. Electrets are a class of electrically-charged materials which can be endowed with a persistent or, at least, transient electrical charge due to their physico/chemical properties. Electrets are attractive for in vivo applications since they can be fabricated from biocompatible polymers and can produce electrical charges without an external power source.

To generate and contain these trapped charges, the electret materials of the present invention preferably are poled. Poling can be performed during manufacture or prior to use and may result in negative or positive charge accumulation on the inner or outer surface of the tubular membrane.

In one embodiment of the invention, nerve guidance channels include positively poled electret material, having a preferable average charge density ranging from about 1 to 100 nanoColoumbs per square centimeter ($nC/cm^2$) and, more preferably, about 21 ($nC/cm^2$). In alternative embodiments of the invention, nerve guidance channels consist of negatively poled electret material, having a preferable average charge density of from about 5 to 30 $nC/cm^2$, with 9 $nC/cm^2$ being a preferred value.

One class of electrets are piezoelectric materials which depend primarily on dynamic mechanical deformation in order to produce transient charge generation on their surface. Charge generation is due to the presence of stable molecular dipoles found throughout the bulk of the polymer.

For example, piezoelectric polyvinylidene fluoride (PVDF) guidance channels have been shown to enhance nerve regeneration as compared to identical but non-piezoelectric PVDF tubes (Aebischer et al., Vol. 436, *Brain Res.* pp. 165–168 (1987). The effects observed are attributed to the transient charges generated as a consequence of random animal movements deforming the channel.

Crystallographers have described various stable forms or phases of PVDF. The alpha phase, which is generally obtained by cooling the melt at atmospheric pressure, has a monoclinic unit cell with chain segments in antipolar orientation, and thus no net dipole moment. The beta phase of PVDF, which displays the highest piezoelectric activity, has an orthorhombic unit cell containing two chains with the same orientation, giving it a permanent dipole moment. To display its piezoelectric properties, PVDF must be anisotropic, i.e., its electrical properties must be quantitatively different for mechanical excitation along different axes. In PVDF as well as other semicrystalline polymer films, the isotropy that generally prevails can be altered by a "poling" process or molecular orientation, usually induced by mechanical stretching, followed by alignment of the permanent dipoles in a direction perpendicular to the plane of the film by an electric field. Upon mechanical deformation, such a polarized piezoelectric material will generate charge.

The use poled PVDF has been found to surpass all other piezoelectric materials tested to date as guidance channels. When compared with unpoled PVDF, the poled material achieved significantly better results (over twice as many myelinated axons after four weeks) as a nerve guidance material. The success of poled PVDF as a nerve guidance channel material appears to lie in its biocompatibility and high piezoelectric activity. The best results have been obtained with tubular PVDF which is poled to generate positive charges on the inner (luminal) surface of the tubes upon mechanical deformation.

Other piezoelectric materials useful in the present invention include polyvinyl chloride, polyvinyl fluoride, collagen, nylon II, polyhydroxybutyrate, poly-γ-benzyl-glutamate, poly-γ-methyl-glutamate, copolymers of trifluoroethylene and such polymers, and derivatives of such polymers.

However, because charge generation in piezoelectric materials is dependent upon movement, it may not be as reliable as those charges generated independently of movement. Without any external stimulation, a non-piezoelectric electret material exhibits a charge storage mechanism consisting primarily of monopolar charges entrapped throughout the polymer. The distribution and stability of this static surface charge are related to the method of fabrication (including poling).

An example of electrical material that can provide persistent electrical charges at the membrane surface is polytetrafluoroethylene (PTFE). In addition, polyethylene, polyamides, polyvinyl chloride, polymethyl methacrylate, polypropylene, polyethylene teraphthalate, and derivatives thereof may be useful materials in forming nerve guidance channels that exhibit persistent charges.

In addition to the use of an electrically-charged material, the lumen of the tubular membrane of the device may be "seeded" or prefilled with a substance that protects, soothes, nurtures, and/or enhances nerve growth therethrough. Useful substances may include, for example, a saline solution or a matrix material, such as laminin, collagen, fibrin, glycosaminoglycan, biologically active factors, such as nerve growth factors and enhancers, or mixtures thereof. Alternatively, the lumen may be seeded with nerve-associated glial cells, such as Schwann cells which are known to stimulate and protect neuronal appendages. The membrane is designed to be impermeable to some of these substances so that they remain within the walls or lumen of the device and, hence, in close contact with the regenerating nerve ends.

Other useful substances include active factors or any diffusible substances with bioactivity that stimulates nerve growth. Useful active factors include, for example, second messenger substances, such as cAMP, or membrane-permeable permanent cAMP analogs, such as 8-bromo cAMP or chlorophenylthio cAMP. A "second messenger" substance is one that initiates a cellular response to a specific signal external to that cell. Second messenger inducers such as forskolin are also useful. In addition, growth factors, such as nerve growth factor, brain-derived growth factor, fibroblast growth factor, and mixtures thereof, are also useful active factors.

The invention further encompasses methods of repairing a severed nerve. In these methods, the nerve guidance channels of the present invention, as described above, are used by locating the severed nerve ends and selecting and providing an appropriately-sized, tubular device for the repair. The cut ends of the nerve are then gently drawn into channel by manual manipulation or suction, placed in optimal proximity and then secured in position without undue trauma by sutures through the channel, or by a biocompatible adhesive (e.g., fibrin glue) or by frictional engagement with the channel. The channel is then situated in the general in vivo location of the nerve. Antibiotics can be administered to the site, and the wound is then closed.

The nerve repair method of the present invention may further include splitting of the channel along a line of weakness and removing it from the nerve ends after they have regenerated and joined. Alternatively, the device may be allowed to biodegrade in vivo.

With time, implanted nerve guidance channels of the present invention have been found to contain regenerated nerve cables. In particular, channels composed of poled electret material were observed to enhance the regeneration of more morphologically normal myelinated nerves when compared with channels composed of unpoled materials.

The invention will be further understood from the following, non-limiting examples.

EXAMPLE 1

Young female CD-1 mice (25–30 g) (Charles River Lab., Wilmington, Mass.) were housed in temperature and humidity-controlled rooms and received food and water ad libitum. The mice were anesthetized with methoxyfluorane and the left sciatic nerve was exposed through an incision along the anterior-medial aspect of the upper thigh. After retraction of the gluteus maximus muscle, a 3–4 mm segment of nerve proximal to the tibio-peroneal bifurcation was resected and discarded.

A series of materials were then tested as nerve guidance channels. The materials were all tubular in shape and 6 mm long. The nerve stumps were anchored 4 mm apart within the tubes using 10–0 nylon sutures placed through holes 1 mm from each channel end. For each material, at least six channels were implanted for a period of four weeks. A further set of control animals underwent nerve resection as described apart, and their section sites were closed without implantation of any guidance material. Aseptic surgical technique was maintained throughout the procedures, which were performed with the aid of an operating microscope.

EXAMPLE 2

A variety of non-electret materials were used as tubular guidance channels for comparison purposes. These non-electret materials included polyethylene (Clay Adams, Parsippany, N.J.), TeflonT (Gore, Flagstaff Ariz.), silicone (Silmed, Taunton, Mass.), and acrylic copolymer (Amicon XD-50 tubing, Lexington, Mass.). In addition, non-polarized PVDF was compared with identical PVDF tubing which had undergone poling.

EXAMPLE 3

Piezoelectric guidance materials were manufactured from pellets of homopolymeric PVDF (Solef XION ®, Solvay & Cie, Brussels, Belgium). The pellets were extruded into tubes with an outer diameter (OD) of 2.5 mm and an internal diameter (ID) of 1.85 mm. The extruded tubes were stretched 3.5 times along their axes at a temperature of 110° C. and at a rate of 1 cm per minute. This stretching process transform the alpha non-polar crystalline phase into the beta polar crystalline phase. The tubes were then annealed by maintaining the tension on the tubes for 3 hr at 110° C. The final OD and ID were 1.25 mm and 0.87 mm, respectively.

Some tubes were then cut and poled under an electric field to permanently orient the molecular dipoles of the beta phase. A thin wire inserted in the lumen of the stretched PVDF tubes served as an inner electrode and a circumferentially regularly oriented array of steel needles served as the outer electrode. The outer electrodes were connected to the positive output of a voltage supply (Model 205-30P, Bertran Associates Inc., Syosset, N.Y.), and the inner electrode was grounded. The voltage was increased gradually over 2 hr until it reached 21 kv and was then maintained for 12 hr. A second set of tubes was poled by connecting the positive output of the voltage supply to the inner electrode and grounding the outer electrode. In both cases, this poling procedure resulted in the generation of surface electrical charges upon mechanical deformation of the tube. Electrical charge distribution was dependent on the local mechanical strain on the tube; the pattern of electrical charges is opposite in the tubes prepared with reversed polarity.

In order to determine the piezoelectric activity of the poled tubes, their outer surface was coated with a thin layer of silver paint and the inner electrode was repositioned. A vertical deflection of 1 mm was induced in the center of each tube by a rotating cam connected to a DC micromotor. The average charge generated by the tubes poled with positive or negative external electrodes was 200–300 pC. These measurements translated into polarization constants ranging from about 10 to about 15 picoColumbs per Newton for the poled PVDF tubes. Unpoled tubes did not generate a detectable charge upon deformation.

Both poled and unpoled PVDF tubes were washed in acetone, rinsed several times with saline, and cleaned ultrasonically before being sterilized in an ethylene oxide gas chamber at 40° C.

EXAMPLE 4

Electret tubes of PTFE were submitted to a corona poling procedure in order to inject electrical carriers into them. A brass wire fitted into the lumen of the tube was used as a reference electrode. A circumferential array of regularly-spaced, steel needles connected to a high voltage D.C. power supply, at a distance of 2 mm from the outer wall of the tube, served to generate the high intensity electric field required for electret preparation. The outer electrode array was connected to the positive output of the power supply with the inner electrode grounded during positive corona discharge, polarities were reversed for negative corona discharge. A 6 mm long positively or negatively poled or unpoled PTFE tubes using single 10-0 nylon sutures. The PTFE tubes were prefilled with physiologic saline in order to prevent trapping of air bubbles within their lumens. Cohorts of 5 animals were implanted with PTFE electret tubes and control PTFE tubes (not submitted to electrical poling).

The corona poling was performed at a relatively high temperature (150° C.) in order to obtain electrets with high charge storage capabilities. At high temperatures, it is possible for the charge carriers to achieve greater depths of penetration into the polymer bulk, although penetration depth rarely exceeds a few microns. The applied voltage was gradually increased to a level of 14 KV and maintained at that voltage for 20 min at 150° C.

The net surface charge density on the outer surface of each electret tube was measured using an induction-based method. A capacitative probe was placed 2 mm from the outer surface of the electret tube and connected to an electrometer (Keithley 610 C, Cleveland, Ohio). When exposed to the electric field produced by the electret, the probe acquires a charge derived from the capacitance at the input of the electrometer. The meter voltage is thus directly related to the quantity of charge trapped in the electret. The average charge density measured for positively poled tubes was 21 nanoCoulombs per square centimeter ($nC/cm^2$); and for negatively poled tubes, it was 9 $nC/cm^2$ The different charge density achieved in otherwise identical PTFE samples can be attributed to the limited penetration of negative charges into PTFE films. All tubes were cleaned and sterilized identically prior to implantation.

EXAMPLE 5

At retrieval time, the animals were deeply anesthetized and perfused transcardially with 5 ml of heparinized phosphate-buffered saline (PBS) followed by 10 ml of a fixative containing 3.0% paraformaldehyde and 2.5% glutaraldehyde in PBS at pH 7.4. The operative site was reopened and the guidance channel and segments of the native nerve at either channel end were removed. The specimens were then post-fixed in a 1% osmium tetroxide solution, dehydrated and embedded in Spurr resin. Transverse sections taken at the midpoint of the guidance channel were cut on a Sorvall MT-5000 microtome (E. I. Dupont Deneneus & Co., Wilmington, Del.). The sections (1 micron thick) were stained with toluidine blue. Whole mounts of nerve were displayed on a video monitor through a Zeiss IM35 microscope.

Nerve cable cross-sectional area and the number of myelinated axons were determined with the aid of a graphic tablet at a final magnification of 630x. The Wilcoxon Rank-sum test was used to assess statistical differences ($p < 0.05$) between the various populations. All values are presented as means % standard error of the mean.

EXAMPLE 6

FIG. 2 shows toluidine blue-stained transverse sections of nerve regenerated at the midpoint of unpoled (A, B), negatively poled (C, D), and positively poled (E, F) PTFE tubes 4 weeks post-implantation. There were numerous myelinated axons surrounded by a fine epineurial sheath in poled tubes. Macrophages are often noted lining the regenerated cables and the inner wall of the guidance channel. Presumptive Schwann cells and numerous microfascicles surrounded by perineurial-like tissue, and numerous unmyelinated axons and myelinated axons at various stages of myelination, can also be observed. Several mast cells are seen within the regenerated cable.

EXAMPLE 7

Figure 3:
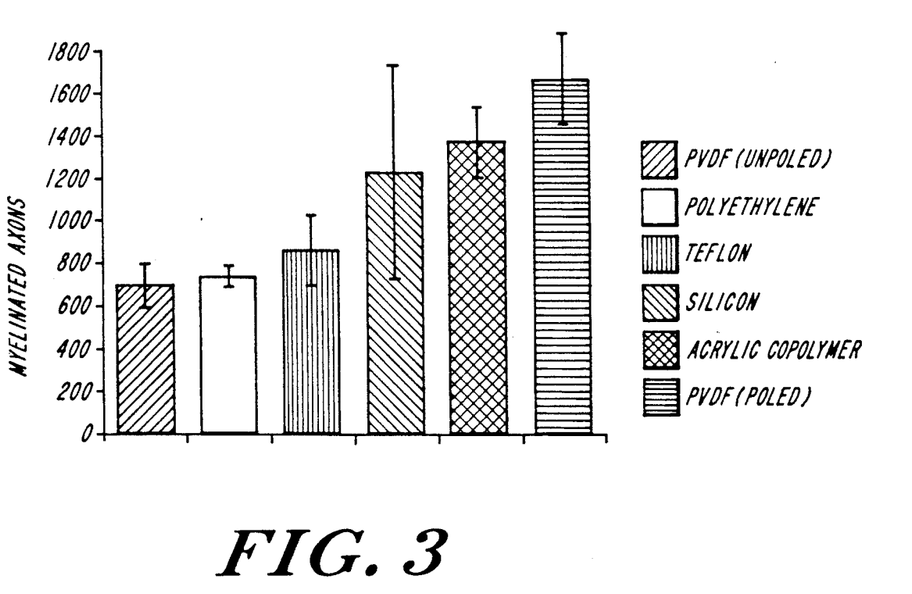
FIG. 3 is a comparative graph of the regenerative capabilities (in terms of numbers of myelinated axons) of various piezoelectric and non-piezoelectric nerve guidance materials.

The results of the comparative studies using piezoelectric and control channels are shown in graphic form in FIG. 3. The number of myelinated axons found upon reexposure after four weeks for each of the tested guidance materials is shown. peripheral nerve regeneration was dramatically enhanced by the use of piezoelectric guidance channels which generated either transient positive or negative charges on their inner surface. Nerves regenerated in poled PVDF tubes contained significantly more myelinated axons and displayed more normal morphological characteristics than nerves regenerated in unpoled tubes. When compared to all other materials tested, the poled PVDF tubes contained the highest number of myelinated axons at four weeks, and the regenerated axons displayed greater diameter and myelin sheath thickness.

Upon reexposure, all retrieved guidance channels were covered by a thin tissue layer which did not reduce the translucence of the PVDF tubes. A cable bridging the nerve stumps was observed in all implanted tubes. All cables were surrounded by an a cellular gel and were free from attachment to the guidance channel wall. In stark contrast, mice with no guidance channel showed complete nerve degeneration.

Nerve cables regenerated in poled and unpoled PVDF tubes differed considerably with respect to their cross-sectional area, relative tissue composition and number of myelinated axons. The cross-sectional area of the regenerated cables at the midpoint of the poled PVDF guidance channels were significantly larger than those regenerated in unpoled PVDF channels (4.33+/−1.25 versus 2.35+/−1.17 mm$^2 \times 10^{-2}$; p<0.05). The cables were delineated by an epineurium composed mainly of fibroblasts and collagen fibrils which surrounded numerous fascicles containing myelinated and nonmyelinated axons and Schwann cells. The results are summarized in TABLE 1.

TABLE 1

|  | Poled | Unpoled |
|---|---|---|
| Myelinated Axons | 1,742 +/− 352 | 778 +/− 328 |
| Fascicular Area* | 71.2 +/− 3.9 | 65.2 +/− 5.1 |
| Epineurial Area* | 19.0 +/− 4.0 | 28.0 +/− 6.0 |
| Blood vessel Area* | 9.8 +/− 3.3 | 6.8 +/− 3.2 |

*Relative surface area of the different nerve cable components in percent.

As shown above, the relative percentage of fascicle area was significantly greater in poled tubes whereas the relative percentage of epineurial tissue was significantly smaller. Although the relative area of blood vessels was higher in poled tubes, the difference was not statistically significant. Most importantly, the nerves regenerated in poled PVDF tubes contained significantly more myelinated axons than those in unpoled PVDF tubes (1,742+/−352 versus 778+/−328; p<− than 0.005).

EXAMPLE 8

The cross-sectional area of the regenerated cable, the total blood vessel area, and the number of myelinated axons and blood vessels were measured with a Zeiss IM 35 microscope interfaced with a computerized morphometric system (CUE-2, Olympus, Lake Success, N.Y.). The Mann-Whitney rank sum test was used to assess statistical difference between the various populations. The results are shown in TABLE 2.

TABLE 2

|  | Channel Type | | |
|---|---|---|---|
|  | Positive | Negative | Unpoled |
| Cable Area (× 10$^4$ mm$^2$) | 16.7 +/− 1.5 | 12.5 +/− 1.4 | 10.2 +/− 1.2 |
| Number Myelinated Axons | 2,301 +/− 206 | 2,118 +/− 181 | 1,544 +/− 160 |

The cross-sectional area of nerves regenerated in positive poled PTFE channels was significantly greater than nerves regenerated in negatively poled and unpoled PTFE channels, as shown above in TABLE 2 and in FIG. 2. Cables regenerated in negatively poled channels were larger than those regenerated in unpoled channels, although the difference was not statistically significant. The ratio of blood vessel area to total cable area was greater in both poled channels as compared to unpoled channels. The number of myelinated axons regenerated in positively and negatively poled channels was significantly greater than the number seen in unpoled channels but were similar to one another. Qualitatively, the geometry of the myelinated axons regenerated in both types of poled channels appeared to be more similar to those seen in normal nerves than those in unpoled channels.

EXAMPLE 9

In order to determine whether electrically-charged materials can influence nerve cell process extension, axonal sprouting, and neuronal differentiation in vitro, cells from a pure mouse neuroblastoma cell line, Nb2a (American Tissue Type Collection), were cultured directly on thin, transparent, polymer films (substrates) of piezoelectric material. The polymer films were either poled (i.e. piezoelectric) or unpoled (i.e. non-piezoelectric) polyvinylidene fluoride (PVDF). Nb2a cells were used for these neuronal differentiation studies because, except for their neoplastic nature, Nb2a cells in tissue culture display differentiation patterns resembling those of neural crest cells in the developing brain. Twenty-eight mm diameter discs of biaxially stretched PVDF (Kynar ®, Penwalt Corp., King of Prussia, Pa. USA) and 40 μm thick biaxially stretched film (Solef ®, Solvay & Cie, Brussels, Belgium) were glued to polystyrene rings to create tissue culture dishes. In this configuration, the poled PVDF acted as a highly sensitive mechanoelectrical transducer and generated charges in response to minute vibrational forces.

The Nb2a cells were cultured in 75 cm$^2$ flasks in DMEM containing 10% FCS, penicillin G (100 U/ml), and streptomycin (100 μg/ml). Aliquots (1 ml containing 10$^4$ cells) were plated on sterile PVDF dishes under 3 media conditions: 1) DMEM/10% fetal calf serum (FCS); 2) serum-free media with no attachment factors (N2(−); or 3) serum-free media with attachment factors (N2(+)) derived by preconditioning the dishes for 18 hr in DMEM/10% FCS. Experimental dishes were maintained on the same incubator shelf at 35° C. in a humidified atmosphere of 5% $CO_2$/95% air. Three dishes each of unaxial and biaxial poled and unpoled PVDF type were plated in parallel for the 3 media conditions.

Under open curcuit condition, piezoelectric output can be measured as the voltage across the film. When filled with fluid and placed in the standard tissue culture incubator used in the study, tissue culture substrates made from poled PVDF polymer films generated peak average charge densities of 0.8 picoCoulombs/cm$^2$ at 1200 hz. when placed on standard incubator shelves. Unpoled substrates showed no output. Electron spectroscopy for chemical analysis (ESCA) and a comprehensive wettability profile revealed that poled and unpoled PVDF surfaces were chemically indistinguishable.

Figure 4A:
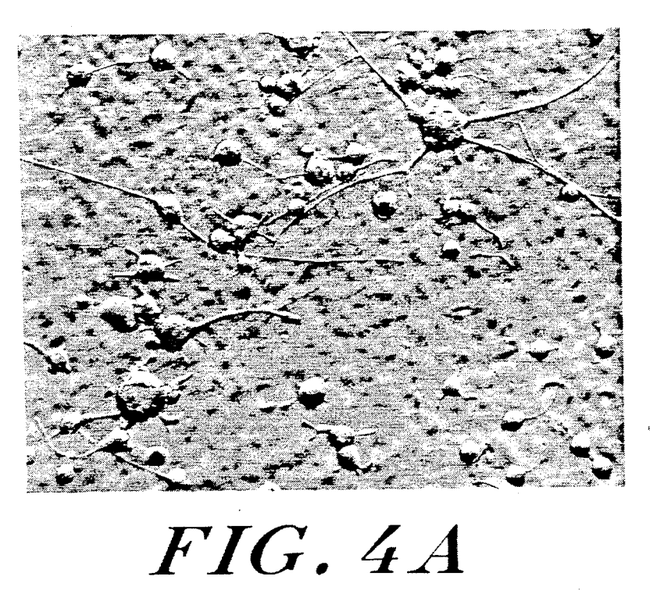
FIG. 4 shows light micrographs of neuroblastoma cells plated on (A) poled or (B) unpoled biaxial PVDF after 96 hours in serum-free N2(+) medium.
Figure 4B:
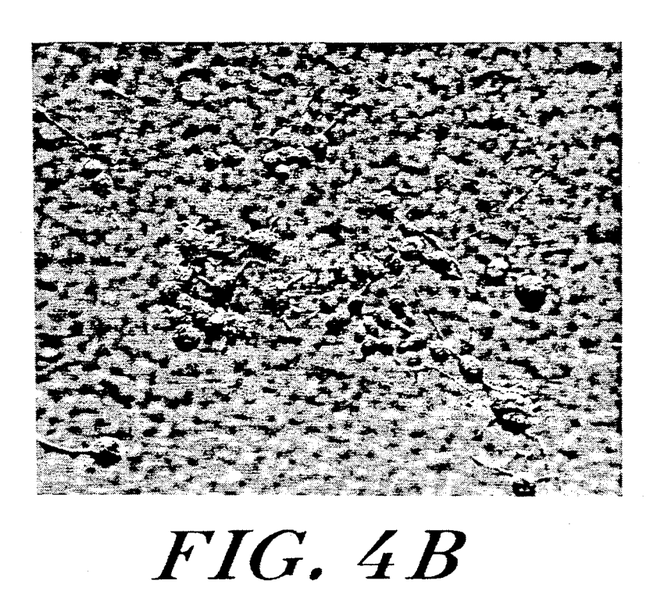

Neurite outgrowth and differentiation were analyzed 24, 48, 72 and 96 hr after plating. FIG. 4 shows light micrographs of cells plated on (A) poled or (B) unpoled biaxial PVDF after 96 hr in serum-free N2(+) medium. A significantly greater percentage of cells grown on piezoelectric substrates exhibited differentiation at all time periods for both media conditions. Note in FIG. 4(A) that neurites radiate in all directions, and many cells have two or more processes.

Figure 5:
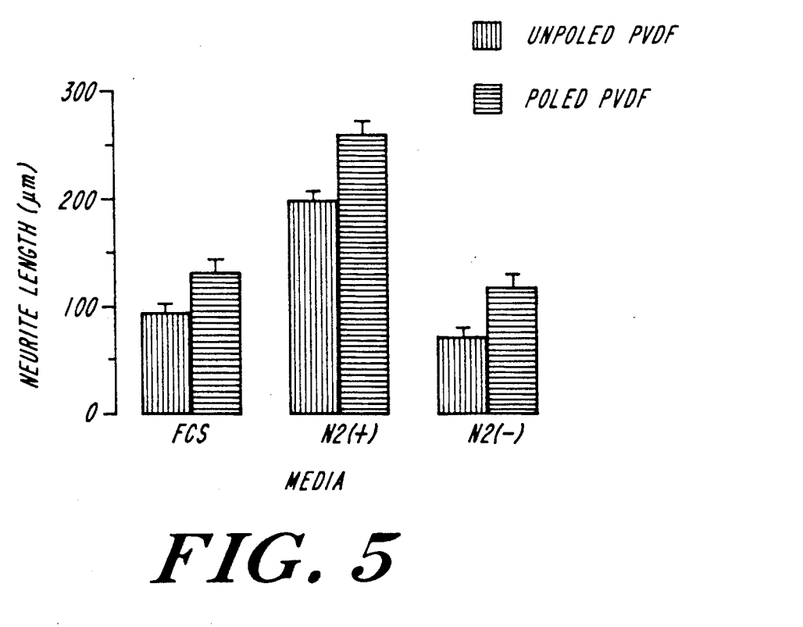
FIG. 5 are histograms demonstrating neurite outgrowth of neuroblastoma cells observed after 96 hours in serum-containing and serum-free culture media and under optimal (i.e. N2(+) media) and suboptimal (i.e. N2(−) media) plating conditions.

Neurite lengths were also significantly greater on poled substrates. The histograms in FIG. 5 show that neurite outgrowth was also observed after 96 hr in serum-containing and serum-free culture media and under optimal (i.e. N2(+) media) and suboptimal (i.e. N2(−) media) plating conditions. Neurite lengths were assessed by randomly measuring 30 neurites for cells on each PVDF dish using a computerized image analysis system. As expected, a greater percentage of cells grown in serum-free media showed outgrowth, but poled substrates always induced significantly more outgrowth than poled substrates.

These results demonstrate that electrically-charged substrates enhance process extension and accelerate the differentiation of mammalian nerve cells. These substrates induce substantially higher levels of neuronal differentiation and neurite outgrowth than do electrically neutral substrates. Such effects are the result of piezoelectric activity rather than the result of changes in substrate surface structure or chemistry of the substrate because: 1) results were similar for isotropic and anisotropic PVDF obtained from separate sources; and 2) ESCA and contact angle profiles reveal indistinguishable chemical compositions and wettability profiles, respectively, for poled and unpoled material.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A medical device for use in regenerating a severed nerve, the device comprising an implantable, tubular, electrically-charged membrane having openings adapted to receive the ends of said severed nerve and a lumen having a diameter ranging from about 0.5 millimeters to about 2.0 centimeters to permit regeneration of the nerve therethrough, said membrane being fabricated such that an electrical charge is exhibited at the inner surface of said membrane to stimulate regeneration by axonal sprouting and process extension.

2. The device of claim 1 wherein said membrane comprises a polymeric material.

3. The device of claim 1 wherein said membrane has an average charge density of about 1 to 100 nanoColoumbs/cm$^2$.

4. The device of claim 3 wherein said electret material is polarized such that a positive charge is generated at said inner membrane surface.

5. The device of claim 3 wherein said electret material is polarized such that a negative charge is generated at said inner membrane surface.

6. The device of claim 1 wherein the thickness of the membrane ranges from about 0.05 to about 1.0 millimeter.

7. The device of claim 1 wherein the membrane is permeable to solutes having a molecular weight of about 100,000 daltons or less.

8. The device of claim 1 wherein the membrane is impermeable to fibroblasts and other scar-forming connective tissue cells.

9. The device of claim 1 wherein said membrane comprises an electret material.

10. The device of claim 9 wherein said surface charge of said material is persistent.

11. The device of claim 10 wherein said electret material is selected from the group consisting of polytetrafluoroethylene (PTFE), polyvinylchloride, polyethylene, polyamides, polymethyl methacrylate, polypropylene, polyethylene terapthalate, and mixtures thereof.

12. The device of claim 11 wherein said electret material comprises polytetrafluoroethylene.

13. The device of claim 9 wherein said surface charge of said material is transient.

14. The device of claim 13 wherein said membrane comprises a piezoelectric material.

15. The device of claim 14 wherein said piezoelectric material has a polarization constant ranging from about 0.5 to about 35 picoColoumbs per Newton.

16. The device of claim 15 wherein said piezoelectric material has a polarization constant ranging from about 1 to about 20 picoColoumbs per Newton.

17. The device of claim 14 wherein said piezoelectric material comprises a material selected from the group of polyvinylidene fluoride, polyvinyl fluoride, polyvinyl chloride, collagen, nylon 11, polyhydroxybutyrate, poly-$\gamma$-benzyl-glutamate, poly-$\gamma$-methyl-glutamate, copolymers of trifluoroethylene and such polymers, and derivatives of such polymers.

18. The device of claim 17 wherein said piezoelectric material comprises polyvinylidene fluoride.

19. The device of claim 18 wherein said polyvinylidene fluoride material has a chain length of about 2,000 to about 15,000 repeat units.

20. The device of claim 18 wherein said polyvinylidene fluoride material has an orthorhombic unit cell structure containing two chains with the same orientation and, consequently, a permanent dipole moment.

21. The device of claim 20 wherein said piezoelectric material comprises polyvinylidene fluoride exhibiting an alignment of the permanent dipoles and a polarization constant of about 1 to about 20 picoColoumbs per Newton.

22. A method for repairing a severed nerve, said comprising:

providing a protective medical device including an implantable, tubular, biocompatible, electrically-charged membrane, said membrane having opening adapted to receive the ends of a severed nerve and a lumen having a diameter ranging from about 0.5 millimeters to about 2.0 centimeters to permit regeneration of the nerve therethrough, said electrically-charged membrane being fabricated such that an electrical charge is exhibited at the inner surface of said membrane to stimulate axonal sprouting and process extension;

placing said severed nerve ends in proximity to each other within said lumen; and securing said nerve ends to said device.

23. The method of claim 22 wherein the step of securing said nerve ends further comprises suturing said nerve ends to said membrane.

24. The method of claim 23 wherein the step of securing said nerve ends further comprises securing said nerve ends with an adhesive.

25. The method of claim 23 wherein said nerve ends are secured by friction.

26. The method of claim 22 further comprising the steps of:

splitting said tubular membrane along a line of weakness; and removing said split tube from said nerve ends after said nerve ends have joined.

27. The method of claim 22 wherein said method further comprises the step of filling said lumen with saline before said placing step.

28. The method of claim 27 wherein said filling step comprises filling said lumen with a matrix material selected from the group of laminin, collagen, and glycosaminoglycan.

29. The method of claim 27 wherein said filling step comprises seeding said lumen with a nerve growth factor.

30. The method of claim 27 wherein said filling step comprises seeding said lumen with Schwann cells.

31. The method of claim 22 wherein said method further comprises, after the securing step, the step of allowing said device to undergo biodegradation in vivo.

32. The method of claim 22 wherein said providing step comprises providing a membrane having an average charge density of about 1 to 100 nanoColoumbs/cm$^2$.

33. The method of claim 22 wherein said providing step comprises providing a membrane that is permeable to solutes having a molecular weight of about 100,000 daltons or less.

34. The method of claim 22 wherein said providing step comprises providing a membrane that is impermeable to fibroblasts and other scar-forming connective tissue cells.

35. The method of claim 22 wherein said providing step comprises providing a membrane having a thickness ranging from about 0.05 to about 1.0 millimeter.

36. The method of claim 22 wherein said providing step comprises providing a membrane including an electret material.

37. The method of claim 36 wherein said providing step comprises providing a membrane including a positively poled electret material.

38. The method of claim 36 wherein said providing step comprises providing a membrane including a negatively poled electret material.

39. The method of claim 36 wherein said providing step comprises providing a membrane including an electret material having a persistent surface charge.

40. The method of claim 36 wherein said providing step comprises providing a membrane including an electret material selected from the group consisting of polytetrafluoroethylene (PTFE), polylvinylchloride, polyethylene, polyamides, polymethyl methacrylate, polypropylene, polyethylene terapthalate, and mixtures thereof.

41. The method of claim 40 wherein said providing step comprises providing a membrane including polytetrafluoroethylene.

42. The method of claim 36 wherein said providing step comprises providing a membrane including an electret material with a transient charge.

43. The method of claim 42 wherein said providing step comprises providing a membrane including a piezoelectric material.

44. The method of claim 43 wherein said providing step comprises providing a membrane including a piezoelectric material having a polarization constant ranging from about 0.5 to about 35 picoColoumbs per Newton.

45. The method of claim 44 wherein said providing step comprises providing a membrane including a piezoelectric material having a polarization constant ranging from about 1 to about 20 picoColoumbs per Newton.

46. The method of claim 43 wherein said providing step comprises providing a membrane including a piezoelectric material selected from the group of polyvinylidene fluoride, polyvinyl fluoride, polyvinyl chloride, collagen, nylon 11, polyhydroxybutyrate, poly-γ-benzyl-glutamate, poly-γ-methyl-glutamate, copolymers of trifluoroethylene and such polymers, and derivatives of such polymers.

47. The method of claim 46 wherein said providing step comprises providing a membrane including polyvinylidene fluoride.

48. The method of claim 47 wherein said providing step comprises providing a membrane including polyvinylidene fluoride having a chain length of about 2,000 to about 15,000 repeat units.

49. The method of claim 47 wherein said providing step comprises providing a membrane including polyvinylidene fluoride exhibiting an orthorhombic unit cell structure containing two chains with the same orientation and, consequently, a permanent dipole moment.

50. The method of claim 49 wherein said providing step comprises providing a membrane including polyvinylidene fluoride exhibiting an alignment of the permanent dipoles and a polarization constant of about 1 to about 20 picoColoumbs per Newton.

* * * * *